United States Patent [19]

Malinouskas

[11] 4,194,179

[45] Mar. 18, 1980

[54] ACTIVE ANTENNA FOR MEDICAL TELEMETRY MONITORING SYSTEMS

[75] Inventor: Donald Malinouskas, Norton, Mass.

[73] Assignee: Becton, Dickinson & Company, East Rutherford, N.J.

[21] Appl. No.: 852,954

[22] Filed: Nov. 18, 1977

[51] Int. Cl.² .................. G08C 15/00; H04B 3/56; H04Q 5/00

[52] U.S. Cl. .................. 340/211; 325/308; 325/367; 340/312

[58] Field of Search .................. 333/80 T, 11, 8; 330/28 T; 340/312, 150, 177 R, 182, 211, 188 CH; 179/15 AD, 170 D, 170 T; 325/464, 308, 305, 365, 367

[56] References Cited

U.S. PATENT DOCUMENTS

| | | | |
|---|---|---|---|
| 2,710,314 | 6/1955 | Tongue et al. | 333/8 UX |
| 2,761,135 | 8/1956 | Tongue | 333/8 X |
| 2,815,406 | 12/1957 | Tongue | 333/8 X |
| 3,898,373 | 8/1975 | Walsh | 178/69.1 X |
| 3,909,560 | 9/1975 | Martin et al. | 325/308 X |
| 3,986,498 | 10/1976 | Lewis | 340/188 CH |
| 4,023,104 | 5/1977 | Rheinfelder | 325/308 |

*Primary Examiner*—Donald J. Yusko

[57] ABSTRACT

A telemetry system and associated antenna for monitoring the physiological condition of hospitalized patients. The antenna consists of two separate sections. The first is the antenna pre-amp section and contains passive receiving antenna elements integrated with a transistor amplifier. The second section provides the required circuitry that allows cascading of additional active antennas. Monitoring a number of patients may be accomplished from a receiver located in a central location. The antennas are small for suitability within a hospital environment, yet offer superior signal/noise performance.

19 Claims, 3 Drawing Figures

4,194,179

ACTIVE ANTENNA FOR MEDICAL TELEMETRY MONITORING SYSTEMS

BACKGROUND OF THE INVENTION

The invention relates to the field of telemetry systems for monitoring the physiological conditions of patients within a hospital environment.

Conventional telemetry systems for monitoring a number of patients have typically utilized a passive antenna, such as a conventional whip antenna, mounted on a receiver which displays the data received from the transmitters. Such systems are adequate where all of the beds and ambulatory patients are confined in one area, such as an open ward.

Where the patients have been located in a number of rooms, a separate passive antenna, amplifier and power supply have been required at each location. This necessitates the installation of a large number of system components and creates added expense. Because the antennas cannot be connected in series, couplers are required for even a two-antenna system.

Conventional passive antennas utilized in a multipatient monitoring system must be of substantial length for adequate reception. For example, a typical whip antenna is ordinarily extended about 18 to 36 inches. It is desirable to minimize the space occupied by telemetry systems, and passive antennas are not adaptable to provide good reception unless extended to a significant height.

Passive antennas also have the disadvantage of causing false alarms in the monitoring system as their signal/noise ratio is not always sufficiently high.

Small active antennas including passive reception elements and a signal amplifier in one integrated unit have not been used to advantage in a hospital environment, nor has a combiner been incorporated to allow series cascading of antennas.

SUMMARY OF THE INVENTION

The invention concerns a telemetry system for monitoring the physiological conditions of patients within a hospital, and an antenna specifically adapted for such application.

It is a principal object of the invention to provide a telemetry system for monitoring one or more patients who may be located in different rooms or at a substantial distance from one another without having to employ a separate antenna, amplifier, and power supply at each location.

It is another object of the invention to provide an antenna for use in a hospital environment which features improved signal/noise performance for reception of weak signals and which exhibits superior directional characteristics than antennas presently employed in hospital use.

Still another object of the invention is to provide a system of small physical size and easy installation which is particularly suited for hospital use.

Still another object of the invention is to provide a telemetry system which is cost efficient as compared to previous systems.

In accordance with these objectives, an active antenna is provided having passive receiving elements integrated with a transistor amplifier, and circuitry which allows cascading (series connections) of additional active antennas. This circuitry includes an amplifier stage for additional gain, a coupling transformer for combining two rf signals, and switch selectable attenuators to provide gain control.

The passive elements are tuned to resonate over a narrow frequency, and thereby reject unwanted signals outside of this range. The transmitted signal received by these elements is fed to an antenna preamplifier, and a tapped capacitor parallel resonant circuit couples the amplified rf signal to one input of a rf coupling transformer.

The second input of the transformer is used for connection to other active antennas. The combined signal is coupled to a wideband amplifier circuit for equalizing the stage gain to the total of all external signal losses.

The telemetry system includes one or more active antennas for receiving transmitted signals from monitored patients. The antennas are coupled to a telemetry receiver via coax cable so that telemetered data, such as ECG signals, may be displayed. Operating power for the antennas may be carried through the same cable used for the transmission of the rf signals from the antennas to the receiving system, or from a separate power supply. This saves the cost of additional power lines. Thw improved signal/noise ratio of the active antenna allows the use of fewer antennas than in conventional systems, as weak signals are more likely to be detected from greater distances.

DESCRIPTION OF THE PREFERRED EMBODIMENT

The extended range active antenna system is used to reliably extend the range of operation beyond that obtainable from a single whip antenna, and which does so without the disadvantages associated with conventional passive systems.

Figure 1:
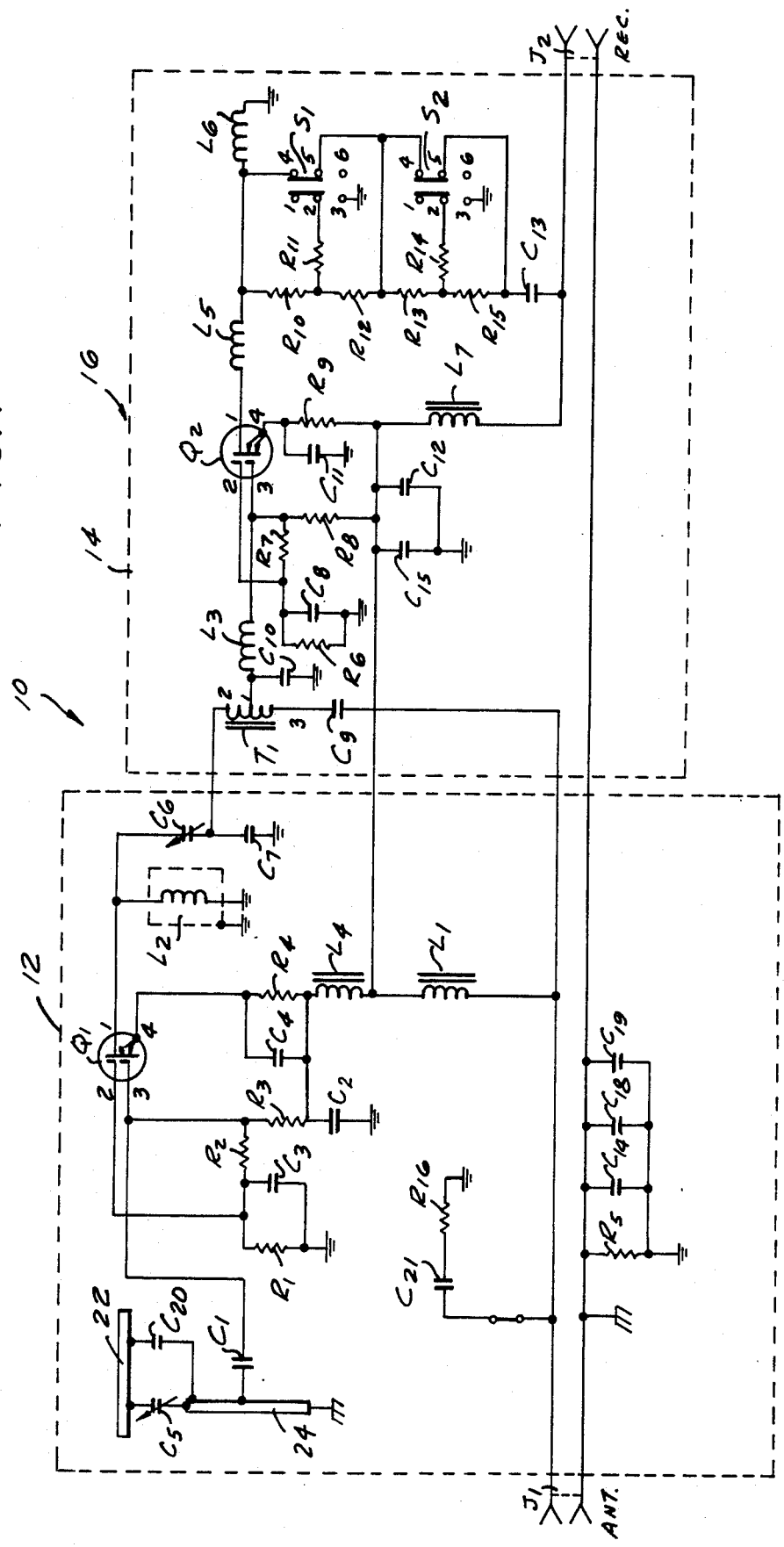
FIG. 1 is a schematic of the active antenna showing the circuitry of the device.

FIG. 1 illustrates the circuitry of the antenna 10, including the antenna pre-amp section 12 and a wide band amplifier section 14. The printed circuit (PC) board 16 is mounted on a metal plate 18 (shown in FIG. 2), and the design of the antenna elements and placement of components is optimized to reduce sensitivities to vertical or horizontal transmission polarization and to provide omnidirectional reception. The device is contained in a plastic housing 20, and is designed to be wall or ceiling mounted. The components located farthest away from the mounting plate 18 comprise the preamplifier circuit containing the passive receiving antenna elements 22 and 24 integrated with a transistor amplifier. The components located adjacent the mounting plate comprise a circuit for cascading additional antennas, a wideband amplifier circuit for combining the two types of input rf signals, and presettable attenuator switches to gain-balance the extended range antenna system. The circuit is comprised, generally of resistors R1-16, capacitors C1-15, 18-21, inductors L1-7, field effect transistors Q1-2, connectors J1-2, switches S1-2, transformer T-1, and the receiving elements.

The transmitted signal received by the passive receiving elements is fed to the antenna preamplifier circuit consisting of capacitors C1, C5, C6, C20, C7, field effect transistor (FET) Q1, inductor L2, and associated components. The receiving elements 22 and 24 are mounted above and perpendicular, respectively, to the metal ground plane, and are positioned a critical distance away from it. These receiving elements are tuned to resonate at 174 to 186 MHz and provide reception of the desired rf signals (channel 7 or 8). Frequencies above and below the desired frequencies are rejected. The single vertical element 24 is mostly inductive and resonates with the capacitance of the top plate, stray capacity and the input capacitance of FET Q1. Capacitor C1 provides coupling from the passive elements to the input of FET Q1. Variable capacitor C5 and capacitor C20 tune the antenna input circuitry to the desired frequency band. FET Q1 is also mounted a critical distance above the ground plate 18 to provide optimum impedance matching between the transistor input (approximately 1,000 ohms) and the passive receiving elements. In this manner, insertion losses introduced by discrete components are avoided.

Resistors R1, R2 and R3 provide bias voltages to gates 1 and 2 of FET Q1 that, in conjunction with resistor R4 and the Q1 transistor characteristics, set the operating drain current to approximately 6 mA for optimum performance. Capacitors C2, C4 and C3 are used for bypass purposes. The received rf signals are then amplified by FET Q1 with the output taken from pin 1 and fed to the rf coupling transformer T1 located in wideband amplifier section of the PC board. Inductor L2 and capacitors C6 and C7 provide impedance matching between the FET Q1 output (approximately 3,000 ohms) and one input terminal transformer T1, while coupling the rf signal. Capacitor C6 is tuned to achieve circuit resonance at midband of the desired frequencies to be received. Additional rejection of unwanted signals is provided by the narrowbandwidth of this impedance matching network.

Located in the wideband amplifier section 14 of the PC board 16, transformer T1 combines the received and amplified rf signals from FET Q1 with the received rf signals from the cascaded active antennas connected via J1. The combined signals are then applied to gate pin 3 of FET Q2 for additional amplification to compensate for signal losses due to connecting cables and external signal couplers or splitters. Capacitor C10, inductor L3 and the input capacitance (6 pf) of FET Q2 form a broad-band impedance matching network that matches the input resistance of FET Q2 (approximately 1,000 ohms) to the output impedance (50 ohms) of transformer T1 pin 1. Broad-band amplifier response is necessary to insure against the accumulation of gain errors incurred in the cascaded system. Capacitor C9 couples the rf signal from the ANTENNA input connector J1 to transformer T1 pin 3. Resistors R6, R7 and R8 provide bias voltages to FET Q2 which, along with FET Q2 characteristics and resistor R9, establish the d-c operating conditions of the stage. The drain current of FET Q2 is designed to be approximately 6 mA. The combined rf signals are amplified by FET Q2 with the output taken from the drain terminal pin 1. Inductor L5 and the output capacitance (approximately 2 pf) of FET Q2 form a broad-band impedance matching network that matches the output resistance of Q2 (approximately 3,000 ohms) to the antenna output impedance (50 ohms). Inductor L6 provides a d-c path for the drain current of FET Q2. Depending upon the positions of attenuator switches S1 and S2, the output signal can pass directly to output receiver connector J2 or through any combination of two attenuator networks. With switch S1 in the position which connects switch pin 2 to 3 and pin 5 to 6, a −3 dB network consisting of resistors R10, R11, and R12 is inserted between connector J2 and the output of the FET Q2. When switch S2 is in the position which connects switch pin 2 to 3 and pin 5 to 6, a −6 dB network consisting of resistors R13, R14, and R15 is inserted between connector J2 and either the output of FET Q2 or the −3 dB attenuator network. A total of 4 switch combinations may be obtained. The selected combination should equalize the stage gain (transistor Q2) to the total of all external signal losses. Equalizing the gain stage should be done without overloading the system, as excessive noise will be produced. Capacitor C13 couples the rf signals from the attenuators to the RECEIVER connector J2. Coax cables connected to J1 and J2 connectors carry both required d-c operating voltages and the input or output rf signals.

Inductors L1 and L7 and capacitors C15 and C12 are used for decoupling purposes. Resistor R16, capacitor C21 and jumper wire W1 are used to obtain a 50-ohm load for transformer T1 pin 3 whenever the ANTENNA input connector J1 is not used (externally connected).

Figure 2:
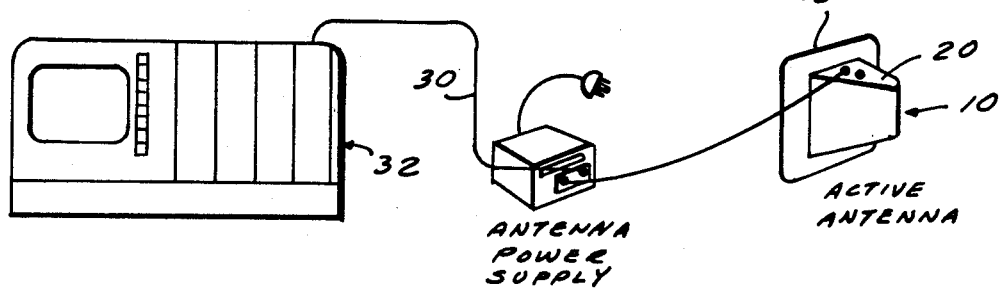
FIG. 2 shows a typical configuration of a single patient telemetry monitoring system.

FIG. 2 illustrates the invention as applied to a single patient telemetry monitoring system. Signals carrying physiological data are transmitted by transmitter 26 and detected by active antenna 10. In this example, a separate antenna power supply 28 is provided. The power supply is designed to supply a regulated output voltage to the components of the extended range system, and is of conventional design. 75-ohm coaxial cable 30 is preferably used to connect the antenna with the power supply, and the power supply to the receiver 32; standard connectors (not shown) are employed. The receiver is also a conventional model, and can display, for example, telemetered ECG data from the patients being monitored.

Figure 3:
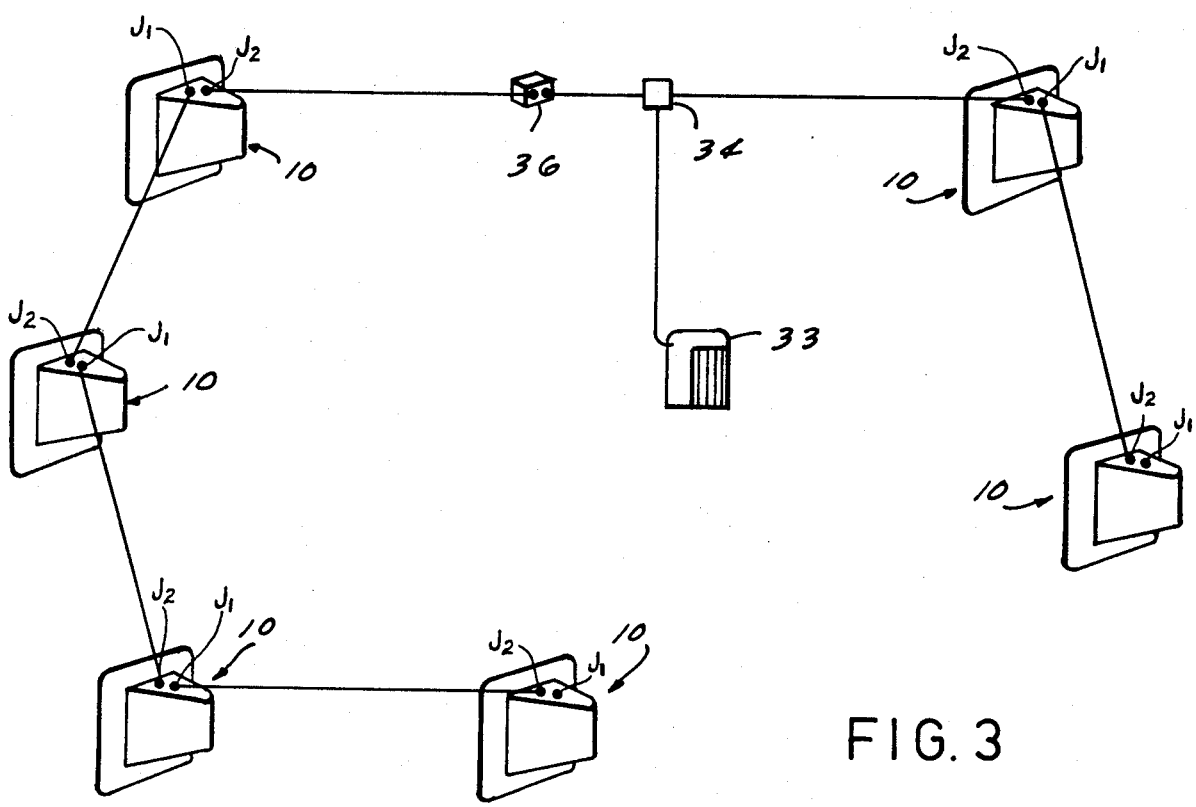
FIG. 3 shows a multipatient monitoring system utilizing six active antennas.

FIG. 3 illustrates a system wherein six active antennas are employed to monitor patients within a given area. Because the antennas contain the required circuitry to allow series cascading, and a wideband amplifier circuit for combining rf signals from both the transmitter and other antennas, the configuration as shown may be assembled. For optimal performance, no more than 5 antennas should be cascaded, however. Due to the greater range of the active antennas, fewer units are needed to monitor a given area as compared with conventional passive systems. A coupler 34 is utilized when a number of branch circuits are required to be coupled into one output branch circuit. A two-way coupler is shown in FIG. 3, although a four-way coupler is employed where there are four branch circuits, for example. Commercially available couplers may be used, such as Model Nos. 7242 or 7244 manufactured by Channel Master. Operating power for the active antennas in this system is supplied by the receiver 33 and carried through the same coax cable used for the transmission of the rf signals from the antennas to the receiver. This saves the cost of additional power lines. Because an active antenna is utilized, the reception elements can be much smaller than those employed in passive systems, and are ordinarily about six inches in length.

An antenna line amplifier 36 is used to provide additional signal gain to compensate for line losses when a single coaxial cable run exceeds 360 feet in length, or to compensate for line/coupler losses when branch-circuit cable runs exceed 160 feet. When required as in FIG. 3, the antenna line amplifier is connected in series with the other antenna components. The amplifier is of conventional design, and preferably consists of a printed circuit board containing a single-stage amplifier and two attenuator gain-balancing switches (not shown). The attenuator switches provide variable gains to compensate for up to an additional 480 feet of cable.

It should be understood that the above description and drawings are illustrative of the invention and not limiting. Alternative antenna structures may be utilized without departing from the spirit of the invention. The scope of the invention should accordingly be determined in light of the appended claims.

What is claimed is:

1. An active antenna assembly for receiving transmitted rf signals representing physiological conditions of a patient, comprising:
   a housing;
   at least one passive reception element within said housing for receiving transmitted rf signals;
   first amplifying means within said housing for amplifying the rf signals received by the reception element;
   combining means within said housing for combining rf signals which have been amplified by said first amplifying means with rf signals from a second antenna assembly;
   first connector means adapted for connecting an output of said combining means to a cable for carrying rf signals; and
   second connector means adapted for connecting a cable carrying rf signals from an output of a second antenna assembly to said combining means.

2. An assembly as described in claim 1 further including a second amplifying means for amplifying the combined signal from said combining means.

3. An assembly as described in claim 2 wherein said first and second amplifying means are field effect transistors.

4. An assembly as described in claim 1 wherein said first and second connector means are adapted for receiving coaxial cable.

5. An assembly as described in claim 1 wherein said first connector means is adapted for receiving the required operating voltage for said assembly from a power source.

6. An assembly as described in claim 1 wherein said at least one reception element is tuned to provide narrow band-width reception.

7. An assembly as described in claim 6 wherein said at least one reception element is tuned to resonate at 174-186 MHz.

8. An assembly as described in claim 1 wherein said combining means is a transformer.

9. An assembly as described in claim 1 wherein said housing is adapted to be mounted to a wall of a hospital room.

10. A telemetry system for monitoring the physiological condition of patients having transmitters for generating rf signals corresponding to a physiological condition, comprising:
    a plurality of antenna assemblies, each of said assemblies including at least one passive reception element for receiving rf signals, first amplifying means for amplifying the rf signals received by the reception element, and combining means for combining rf signals which have been amplified by said first amplifying means with rf signals from another antenna assembly;
    each of said antenna assemblies being connected in series by means of cables connecting respective inputs and outputs of the combining means of the respective antenna assemblies;
    a receiver connected to the output of the combining means of one of the antenna assemblies; and
    a power supply means connected to the output of the combining means of one of said antenna assemblies such that the required operating voltage for each of the series connected antenna assemblies is provided by said power source via the cables connecting the respective combining means.

11. A system as described in claim 10 wherein each of said antenna assemblies includes a second amplifying means for amplifying the combined signals from the respective combining means.

12. A system as described in claim 11 wherein said first and second amplifying means in said respective antenna assemblies are field effect transistors.

13. A system as described in claim 10 wherein said cables are coaxial cables.

14. A system as described in claim 10 wherein said combining means are transformers.

15. A system as described in claim 10 wherein said passive reception elements are tuned to provide narrow bandwidth reception.

16. A system as described in claim 15 wherein said passive reception elements are tuned to resonate at 174-186 MHz.

17. A system as described in claim 10 wherein said passive reception elements are about six inches in length.

18. A system as described in claim 10 wherein each of said antenna assemblies is positioned within a housing.

19. A system as described in claim 10 wherein said receiver includes said power supply means.

* * * * *